United States Patent
Eickhoff et al.

(10) Patent No.: US 7,168,288 B2
(45) Date of Patent: Jan. 30, 2007

(54) HYDROGEN SULFIDE GENERATOR FOR SENSOR CALIBRATION

(75) Inventors: Steven Eickhoff, Plymouth, MN (US); Yuandong Gu, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/384,722

(22) Filed: Mar. 20, 2006

(65) Prior Publication Data

US 2006/0266098 A1 Nov. 30, 2006

Related U.S. Application Data

(63) Continuation-in-part of application No. 11/339,748, filed on Jan. 25, 2006, and a continuation-in-part of application No. 10/908,737, filed on May 24, 2005.

(51) Int. Cl.
*G01N 21/00* (2006.01)

(52) U.S. Cl. ............................................. 73/1.06

(58) Field of Classification Search ............... None
See application file for complete search history.

(56) References Cited

U.S. PATENT DOCUMENTS

| | | | |
|---|---|---|---|
| 4,025,412 A | 5/1977 | LaConti | |
| 4,123,700 A | 10/1978 | LaConti et al. | |
| 4,171,253 A | 10/1979 | Nolan et al. | |
| 4,231,249 A * | 11/1980 | Zuckerman | 73/31.03 |
| 4,387,165 A * | 6/1983 | Youngblood | 436/121 |
| 4,740,473 A * | 4/1988 | Tomlin | 436/79 |
| 6,358,384 B1 * | 3/2002 | Warburton | 204/427 |
| 6,370,940 B2 * | 4/2002 | Warburton | 73/23.21 |
| 2005/0262924 A1 | 12/2005 | Wood et al. | |

* cited by examiner

*Primary Examiner*—Robert Raevis
(74) *Attorney, Agent, or Firm*—Kris T. Fredrick

(57) ABSTRACT

The present invention relates to the use of internally-generated hydrogen sulfide as a calibration gas for hydrogen sulfide sensors. The present invention also relates to an apparatus and methods for self-calibration of hydrogen sulfide sensors.

9 Claims, 3 Drawing Sheets

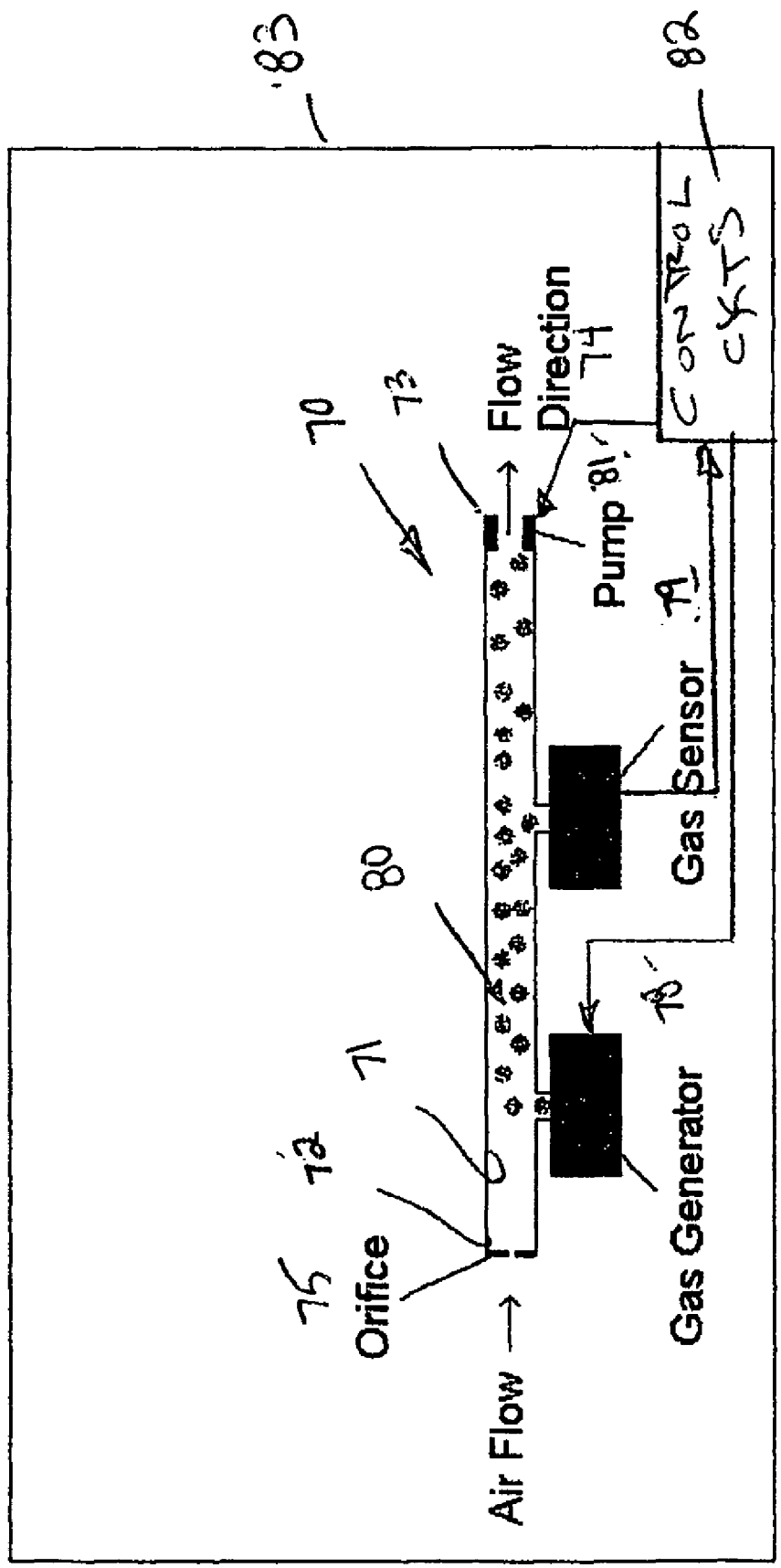

HYDROGEN SULFIDE GENERATOR FOR SENSOR CALIBRATION

CROSS-REFERENCE TO RELATED APPLICATIONS

The present application is a Continuation-In-Part of U.S. application Ser. No. 11/339,748 filed Jan. 25, 2006 and is also a Continuation-In-Part of U.S. application Ser. No. 10/908,737 filed May 24, 2005. The disclosures of both of which are incorporated herein by reference.

BACKGROUND OF THE INVENTION

Gas sensors have been in use for some time to sense various gases such as hydrogen, oxygen, carbon monoxide, etc. One form of a gas sensor is an electrochemical cell that uses a catalytic electrode so that the gas to be detected is either oxidized or reduced with the exchange of electrons. The flow of current due to the oxidation or reduction of the gas is then detected as a measure of the concentration of the gas to be detected.

However, a known problem with gas sensors is that they lose sensitivity over time. For example, the working life of an electrochemical cell is determined by the activity of the cell's catalytic electrode that is used to detect gas within the sensor. This activity is gradually reduced over time by contaminant gases and poisons such that the sensitivity of the sensor drifts downward.

Other types of gas sensors, such as pellistor sensors, biomimetic sensors, and tin oxide sensors that may be formed as thin film, thick film, sintered or MOSFET devices, may have similar problems.

If the instrument into which the gas sensor is built is calibrated regularly, this downward sensitivity drift can be compensated for by adjusting the gain of the gas sensor, and any faulty gas sensors can be replaced immediately. However, if the instrument is in a difficult position to service, or if calibration of the gas sensor is not otherwise freely available, it is often impossible to confirm that the gas sensor is functioning correctly. Therefore, as the gas sensor reaches the end of its working life, the output of the sensing cell may be insufficient to generate an alarm condition. As a result, a situation could arise where toxic levels of gas are present, but the gas sensor is incapable of providing the requisite warning.

A substantial effort has been invested in determining a method by which the function of a gas sensor, such as an electrochemical cell, can be checked without the need for an externally generated calibration gas. For example, it has been proposed to use additional electronic components in order to check conductive pathways through the gas sensor. While such methods can uncover broken connections, they do not provide any information on the condition of the electrodes in terms of their ability to react with the gas to be detected.

When external gas sources are used, gas detectors for industrial applications are normally calibrated to correct for drift. Toxic gas detectors are normally calibrated to measure around the Occupational Exposure Level, which for most toxic gases will be less than 50 ppm, an extremely low level. Because of the difficulty in preparing gas/air mixtures at this dilution, because some toxic gases such as hydrogen sulfide and sulfur dioxide are readily absorbed by the materials used to make the calibration gas cylinder housings, and because the stability of these mixtures can be a problem, calibration gas cylinder have a limited shelf life.

SUMMARY OF THE INVENTION

The present invention relates to the use of internally-generated hydrogen sulfide as a calibration gas for hydrogen sulfide sensors. The present invention also relates to an apparatus and methods for self-calibration of hydrogen sulfide sensors.

According to one aspect of the present invention, a self-calibrating gas sensor includes a hydrogen sulfide detector and a hydrogen sulfide generator, wherein the hydrogen sulfide generator includes a heater and a mixture of a metal sulfide and a solid acid, wherein the mixture is in proximity to the heater such that, when the heater is energized during calibration, the mixture releases an overpressure of hydrogen sulfide to the detector and such that, when the heater is not energized, the mixture releases no substantial overpressure of the hydrogen sulfide to the detector.

According to another aspect of the present invention, a self-calibrating gas sensor includes a gas detector; a hydrogen sulfide generator, wherein the hydrogen sulfide generator includes a heater and a mixture of a metal sulfide and a solid acid, wherein the mixture is in proximity to the heater such that, when the heater is energized during calibration, the mixture releases an overpressure of hydrogen sulfide to the detector and such that, when the heater is not energized, the mixture releases no substantial overpressure of the hydrogen sulfide to the detector; and a continuous housing, wherein the hydrogen sulfide generator and the detector are housed within the continuous housing.

According to another aspect of the present invention, a self-calibrating gas sensor includes a gas detector comprising an electrochemical cell; and, a hydrogen sulfide generator, wherein the hydrogen sulfide generator includes a heater and a mixture of a metal sulfide and a solid acid, wherein the mixture is in proximity to the heater such that, when the heater is energized during calibration, the mixture releases an overpressure of hydrogen sulfide to the detector and such that, when the heater is not energized, the mixture releases no substantial overpressure of hydrogen sulfide to the detector.

According to still another aspect of the present invention, an apparatus includes a gas sensor having at least one gas inflow port, an orifice providing one of calibration flow, or, non-calibration flow; and a source of hydrogen sulfide, the source provides hydrogen sulfide when the orifice provides calibration flow.

According to still another aspect of the present invention, a calibratable gas detector includes a housing, the housing including at least one gas inflow port with an internal gas flow path coupled thereto; a source of hydrogen sulfide in flow communication with the gas flow path; a gas sensor where ambient atmosphere which flows into the gas sensor; a pump coupled to the gas flow path; a multi-state orifice coupled to the inflow port, the orifice having a constricting state which limits flow into the flow path and a second, different, state.

According to still another aspect of the present invention, a method includes providing a limited flow of a selected carrier fluid; diffusing hydrogen sulfide to a sensing region; and sensing a concentration of the hydrogen sulfide.

According to another aspect of the present invention, a method of calibrating a hydrogen sulfide gas sensor includes providing a hydrogen sulfide gas detector and a hydrogen sulfide gas generator adjacent to the hydrogen sulfide detector, wherein the hydrogen sulfide gas generator includes a heating element and a mixture of a metal sulfide and a solid acid in thermal communication with the heating element;

heating the mixture with the heating element to release a known amount of hydrogen sulfide gas; detecting the known amount of hydrogen sulfide gas with the hydrogen sulfide detector to provide an output value from the hydrogen sulfide detector; and calibrating the output value based on the known amount of hydrogen sulfide gas.

BRIEF DESCRIPTION OF THE DRAWINGS

FIG. 4 is a schematic block diagram of a self-calibrating hydrogen sulfide gas detector in accordance with the invention;

DETAILED DESCRIPTION

The present invention relates to internal generation of a hydrogen sulfide reference gas to calibrate a hydrogen sulfide sensor.

Figure 1:
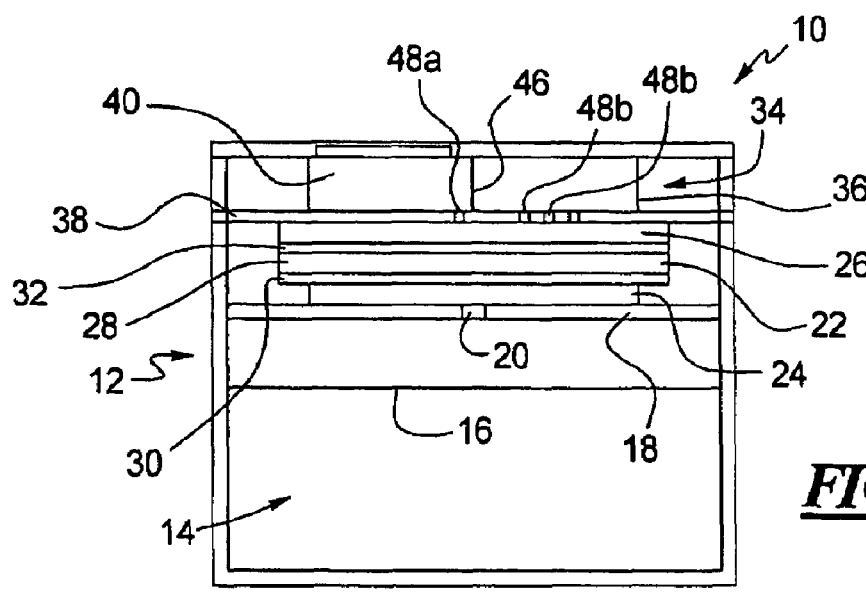
FIG. 1 illustrates a self-calibrating hydrogen sulfide gas sensor according to one embodiment of the present invention.

In one embodiment, shown as FIG. 1, a self-calibrating hydrogen sulfide gas sensor 10 has a housing that, for example, may be in the form of a can 12 that is covered at its open end by a cover. The can 12 and the cover, for example, may be made of nickel plated steel. The can 12 holds a substance 14 such as water or water gel or hydrophilic oxides like silica gel in an antiseptic solution. The substance 14 provides a source of water vapor for the self-calibrating gas sensor 10. As shown in FIG. 1, the substance 14 has a level 16, although the can 12 can contain more or less of the substance 14. Other materials can be used for the substance 14 depending upon the particular application temperature range for the self-calibrating gas sensor 10.

A support plate 18 is provided in the can 12 above the level 16 of the substance 14. The support plate 18 has a hole 20 therethrough to permit the flow of vapor from the substance 14 through the support plate 18. The support plate 18, for example, may be a stainless steel washer.

A hydrogen sulfide detector 22 is supported by the support plate 18. The hydrogen sulfide detector 22, for example, may be in the form of an electrochemical cell. As such, the hydrogen sulfide detector 22 includes lower and upper cell plates 24 and 26, a solid electrolyte membrane 28, and lower and upper catalyst electrodes 30 and 32. The lower and upper cell plates 24 and 26, for example, may be hydrophobic Teflon (TM) disks.

The lower cell plate 24 is sandwiched between the support plate 18 and lower catalyst electrode 30, the lower catalyst electrode 30 is sandwiched between the solid electrolyte membrane 28 and the lower cell plate 24, and the upper catalyst electrode 32 is sandwiched between the solid electrolyte membrane 28 and the upper cell plate 26. The catalyst electrode 30 and 32, for example, may comprise an element from the group Au, Pt, Pd, Ru, Rh, Ir, Os, Ag, etc., or an alloy or mixture of the elements from this group, or porous elements of the group mixed with carbon black, or porous elements of the group mixed with carbon black and Nafion particles. The solid electrolyte membrane 28 may be Nafion or Nafion composite like Nafion/$7SiO_2$-$2P_2O_5$—$ZrO_2$, and Nafion/ZrP particles or the Sandia Polymer Electrolyte Alternative (SPEA) for higher temperature applications. The gas detector 22 may be of the type shown in one or more of U.S. Pat. Nos. 4,025,412, 4,123,700, and 4,171,253.

A hydrogen sulfide generator 34 internally generates hydrogen sulfide gas that is provided to the detector 22 so that the hydrogen sulfide detector can be self-calibrated. The hydrogen sulfide generator 34 includes a hydrogen sulfide generating chamber 36 and a gas diffusion control plate 38. The gas sensor 10 also includes an active charcoal filter 40. The gas diffusion control plate 38 separates the hydrogen sulfide generating chamber 36 and the active charcoal filter 40 from the hydrogen sulfide detector 22 and abuts the upper cell plate 26.

Figure 2:
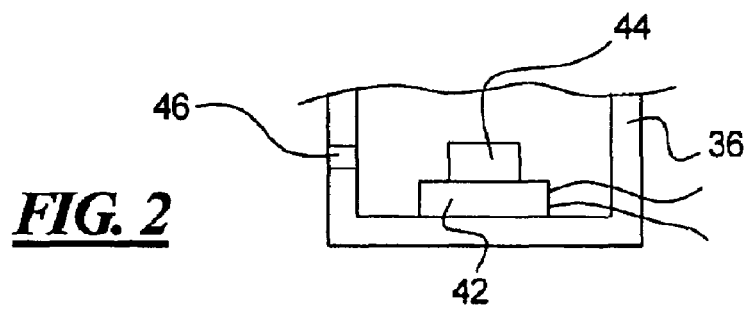
FIG. 2 shows the hydrogen sulfide reference gas generator of the self-calibrating gas sensor shown in FIG. 1 in additional detail.

As shown in FIG. 2, the hydrogen sulfide generating chamber 36 houses a heater 42 and a mixture 44 that is in proximity to the heater 42. The mixture 44, when heated, produces the hydrogen sulfide gas. For example, the mixture 44 includes a metal sulfide and a solid acid that, when the heater 42 is energized, is heated to a known temperature and consequently produces a known overpressure of hydrogen sulfide gas. The overpressure causes the hydrogen sulfide gas to flow through holes 48b in the gas diffusion control plate 38 directly into to the gas detector 22.

Preferred metal sulfides for mixture 44 include, for example, calcium sulfide, zinc sulfide, copper sulfide, and silver sulfide. Suitable solid acids include those that adopt a solid form at temperatures below 50° C. and have a stronger acidity than hydrogen sulfide, such as mineral acids, organic acids, polyacids, and Lewis acids. Preferred solid acids include, for example, citric acid, phtalic acid $C_6H_4(COOH)_2$, benzoic acid, their acidic derivatives, and polyacids, such as, polystyrene sulfonic acid, polyacrylic acid, polyphosphoric acid, polyphosphonic acid, polymaleic acid, and their acidic derivatives. Further, the mixture may be encapsulated to eliminate effects from environmental conditions when the sensor does not need to be calibrated. Preferred encapsulation materials include, for example, polymers, metals, and dielectrics.

Accordingly, when the self-calibrating gas sensor 10 is to be calibrated, the heater 42 is energized to heat the mixture 44 to a predetermined temperature and for a predetermined time that causes the mixture 44 to release an overpressure of the hydrogen sulfide which is supplied to the hydrogen sulfide detector 22. The detector 22 senses the hydrogen sulfide thus generating a reference signal from the lower and upper catalyst electrodes 30 and 32. This signal is used to perform self-calibration. After such self-calibration, the heater 42 is de-energized so that the overpressure of the hydrogen sulfide gas falls to a negligible level. Such self-calibration of the self-calibration gas sensor 10 can be intermittently repeated as desired.

As shown in FIG. 1, the can 12 forms a continuous housing that houses the hydrogen sulfide detector 22 and the hydrogen sulfide generator 34. Accordingly, in this construction of this embodiment, the detector 22 and the hydrogen sulfide generator 34 are not housed in separate and separated housings.

Figure 3:
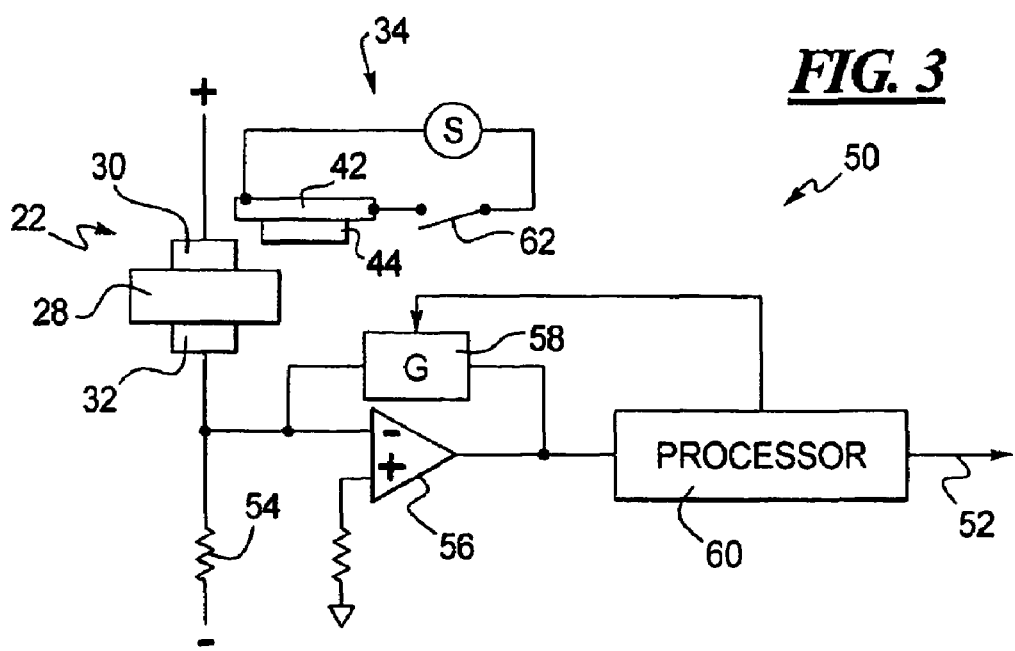
FIG. 3 shows a circuit that can be used in the self-calibration process.

As shown in FIG. 3, a controller 50 provides an output 52 based on the hydrogen sulfide detected by the detector 22 and controls the hydrogen sulfide generator 34 to calibrate the hydrogen sulfide detector 22. The output 52 may be coupled to various devices. For example, the output 52 may be coupled to an alarm indicator to produce a warning when the level of the detected hydrogen sulfide gas exceeds a predetermined limit, or the output 52 may be coupled to an apparatus such as a ventilator to control the effects of the hydrogen sulfide being detected. The self-calibration could be pre-programmed to operate twice a year or once a year. Calibration could also be initiated through pushing an external button. When self-calibration is in process, the controller 50 should provide an alarm/warning that self-calibration is being performed, and that the controller 50 may be out of function momentarily.

The lower and upper catalyst electrodes 30 and 32 are coupled between the terminals of a source through a resistor 54. The junction between the resistor 54 and the hydrogen sulfide detector 22 is coupled to an amplifier 56 having a gain controlling element 58 in a feedback circuit around the amplifier 56. The output of the amplifier 56 is coupled to a processor 60 that provides the output 52, that controls the gain controlling element 58, and that controls a switch 62 to selectively connect a source S to the heater 42 so as to energize the hydrogen sulfide generator 34.

During normal operation, the processor 60 provides the output 52 based on the output of the amplifier 56 and controls the switch 62 so that the switch 62 is open. Thus, the hydrogen sulfide generator 34 is de-energized and the output 52 indicates the level of ambient gas normally being detected by the gas detector 22. This ambient gas normally being detected by the gas detector 22 enters the gas sensor 10 through one or more suitable holes (not shown) in the can 12, flows through the active charcoal filter 40, then flows through one or more holes 48a of the gas diffusion control plate 38 into the hydrogen sulfide detector 22.

During self-calibration, the processor 60 controls the switch 62 so that the switch 62 is closed. Thus, the hydrogen sulfide reference gas generator 34 is energized to produce the hydrogen sulfide reference gas and to provide the hydrogen sulfide reference gas to the hydrogen sulfide gas detector 22 as described above. The processor 60 receives the output of the amplifier 56 and controls the gain controlling element 58 accordingly until the output of the amplifier 56 is at a desired calibration level. Accordingly, the self-calibration gas sensor 10 is calibrated.

The controller 50 may intermittently repeat the above described calibration as many times as necessary or desired. The time periods between such repeated calibrations may be periodic or aperiodic and may be of any length as desired.

The circuit 50 can be mounted as a chip or otherwise on a board or other support within the can 12. The output 52 may then be run to the exterior of the can 12.

Certain modifications of the present invention have been discussed above. Other modifications will occur to those practicing in the art of the present invention. For example, the hydrogen sulfide detector 22 as discussed above may be an electrochemical cell. Alternatively, the detector 22 may be a pellistor sensor, a biomimetic sensor, and a tin oxide sensor, or other gas detector.

Moreover, FIG. 1 illustrates an embodiment of the present invention in which the can 12 forms a continuous housing that houses the hydrogen sulfide detector 22 and the hydrogen sulfide generator 34. However, the hydrogen sulfide detector 22 and the hydrogen sulfide generator 34 may instead be housed in separate and separated housings.

Also, the hydrogen sulfide generating chamber 36 is preferably, although not necessarily, sealed. If sealed, it may be possible for the over pressure in the hydrogen sulfide generating chamber 36 to become excessive. In this case, a suitable pressure relief valve or other compensator may be provided to maintain the over pressure below an acceptable limit.

Also presented is a self-calibrating hydrogen sulfide gas detector, which incorporates a flow path with a gas inlet end and an orifice associated therewith. A hydrogen sulfide generator, which generates hydrogen sulfide as discussed above by heating a mixture of a metal sulfide and a solid acid, as well as a hydrogen sulfide sensor are coupled to the path. Finally, if desired a pump can also be coupled to the path.

To carry out a calibration process, the orifice is moved or switched to a state so that it restricts or constricts the inlet of the flow path. This restricts the flow of ambient atmosphere to the sensor.

The pump and source of hydrogen sulfide can both be activated. The pump, when activated, causes ambient atmosphere to pass a sensing region of the hydrogen sulfide sensor at a reduced flow rate relative to normal operational flow past the hydrogen sulfide sensor. The activated source of hydrogen sulfide generates a known amount of hydrogen sulfide.

Those of skill in the art will understand that additional sensors that measure the ambient temperature, humidity, and pressure can be incorporated to further enhance the calibration process since these variables can affect the perceived concentration of a gas, such as hydrogen sulfide. A filter or selectively permeable membrane can also be provided to cover the inlet of the flow path and prevent an inflow of harmful particulates and gases that might damage the sensor.

The hydrogen sulfide diffuses into the inflowing ambient atmosphere traversing the path. This mixture in turn flows into or through the sensing region of the hydrogen sensor. The sensor responds thereto and generates an output signal corresponding thereto which can be used for calibration and making a determination as to the performance characteristics of the sensor.

In accordance with the invention, a reduced flow rate in a range of 1 to 100 cc/min is particularly advantageous as it reduces the amount of hydrogen sulfide required for the process. This can in turn reduce the size and power consumption of the hydrogen sulfide generator.

A detector which embodies the invention is also self-checking. For example, a determination can be made whether the flow path through which the ambient atmosphere is to be drawn is clear or whether it is exhibiting the symptoms of blockage. Further, it is also possible to determine if the sampling pump is functioning as expected.

In yet another aspect of the invention, the flow path can be restricted by a mechanically movable orifice. The orifice could be moved into a calibration position partly closing the inlet which significantly reduces the gas flow through the flow or sampling path. The orifice can be moved into a normal operational position once the calibration process has been concluded.

In another aspect of the invention, the sample pump could be implemented as a peristaltic, diaphragm pump, or, alternatively, an electronic pump all without limitation.

FIG. 4 illustrates a hydrogen sulfide detector 70 in accordance with the invention. The detector 70 incorporates a flow path 71 with an inlet end 72 and an outlet end 73. In normal operation, ambient atmosphere can flow from the inlet end 72 of the flow path 71 through to the outlet end 73 in a direction 74.

The detector 70 can incorporate an orifice 75 which can exhibit at least two different states. In one state the orifice 75 restricts inflowing ambient atmosphere into the flow path 71.

In this state, illustrated in FIG. 4, ambient atmosphere can be expected to pass through the flow path 71 at a reduced flow rate relative to normal operation. When not carrying out a calibration function, the orifice 75 can be mechanically slid or rotated from the inlet 72.

Alternately, the orifice 75 can electrically assume a non-constricting state. The non-constricting state can be achieved by means of an electrically actuated transducer which will physically move the orifice 75. The orifice 75 could also be switched electronically from a constricting state to a non-constricting state as would be understood by those of skill in the art.

Detector 70 also incorporates a hydrogen sulfide gas generator 78 and hydrogen sulfide gas sensor 79.

The hydrogen sulfide generator 78 can be electrically actuated so as to generate a predetermined quantity of hydrogen sulfide, indicated generally at 80, in the flow path 71. Hydrogen sulfide gas 80 diffuses into the stream of ambient atmosphere flowing in the path 71. A pump 81 can be coupled to outlet 73 to produce a flow of ambient atmosphere and hydrogen sulfide gas 80 through the flow path 71.

Control circuits 82 can be provided to provide electrical signals to actuate the generator 78, receive inputs from the sensor 79 and to actuate pump 81. The detector 71 can be carried in a housing 83 which can also contain a power supply, such as one or more batteries as would be understood by those of skill in the art.

Figure 5:
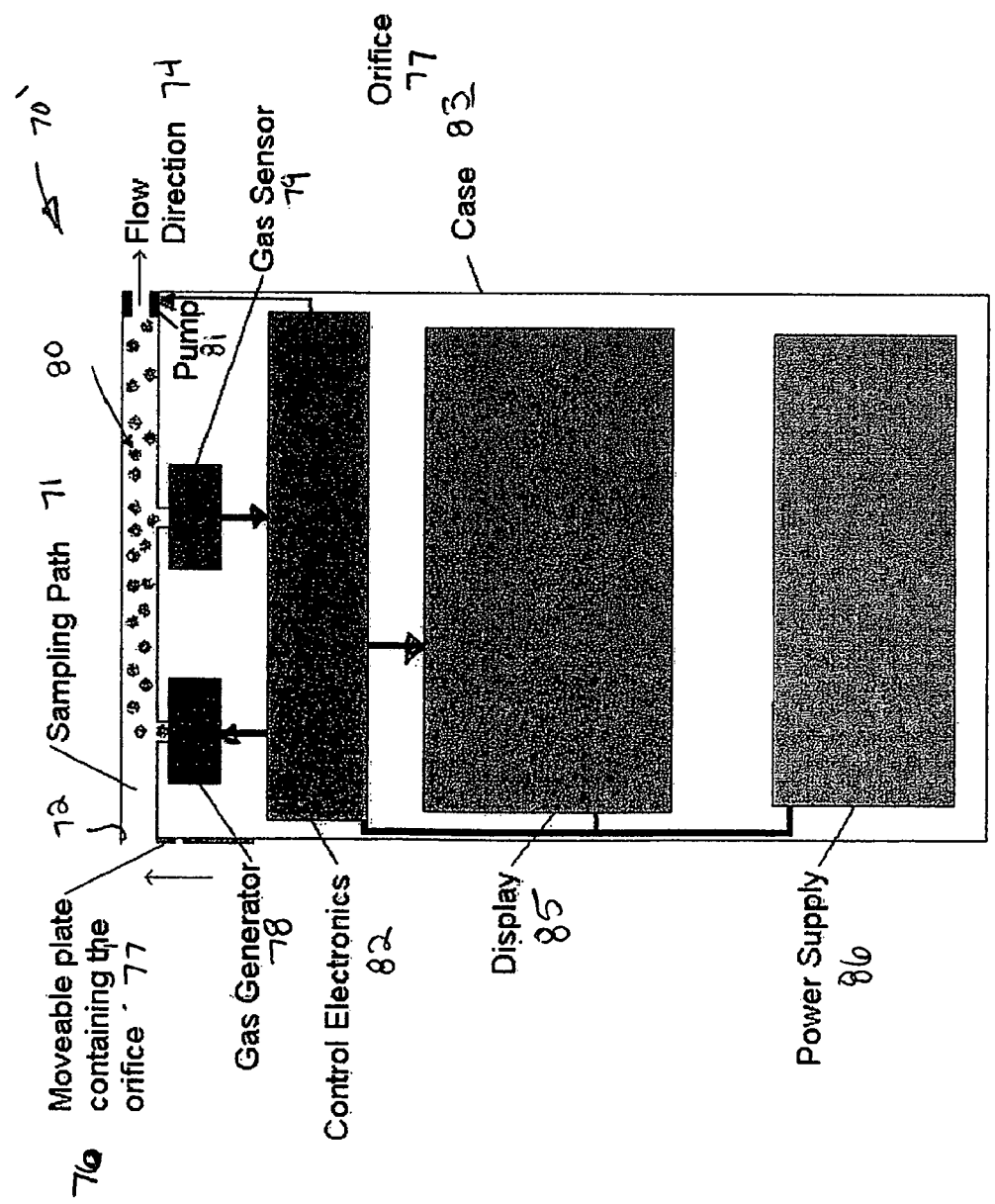
FIG. 5 is a front elevational view of a self-contained, portable, hydrogen sulfide gas detector in accordance with the invention.

FIG. 5 is a front elevational view of a detector 70' which embodies the present invention. Elements of the detector 70' of FIG. 5 which correspond to elements of the detector 71 of FIG. 4 have been assigned the same identification numeral. As illustrated in FIG. 5, in one embodiment of the invention, a movable plate 76 can be provided which has an orifice 77, best seen in FIG. 6.

The plate 76 is movable in first and second directions, generally indicated at 84 relative to flow path 71. In a calibrating or restricting position the plate 76 partly closing flow path 71. Plate 76 permits an inflow of ambient atmosphere only through the orifice 77. When in this state, the control electronics 82 can actuate hydrogen sulfide generator 78 as well as pump 81 which in turn provides a mixture of ambient atmosphere, drawn through opening 77, and hydrogen sulfide 80 from generator 78.

That mixture is presented to hydrogen sulfide sensor 79, via path 71. Hydrogen sulfide 80 can diffuse into or pass by sensor 79 and be detected thereby. Outputs from sensor 79 which are coupled to control electronics 82 provide an electrical signal indicative of the response of the sensor 79 to the hydrogen sulfide 80.

The electronics 82 can carry out either an automatic or a semi-automatic calibration of the sensor 79 in response to the signals received therefrom.

Figure 6:
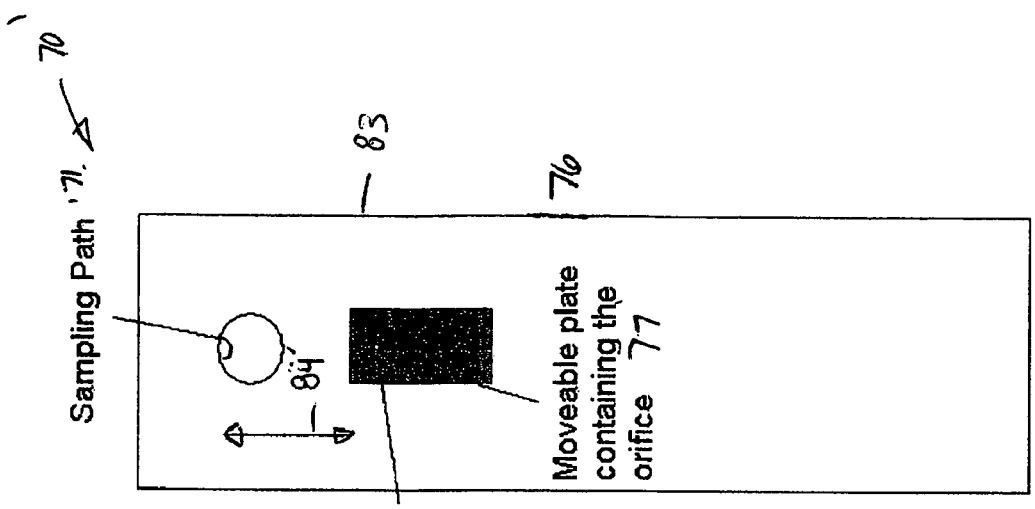
FIG. 6 is a side elevational view of the detector of FIG. 5.

The electronics 82 can actuate display 85 to provide a concentration of the hydrogen sulfide if desired. Alternatively, the display 85 can provide an indication of sensed ambient gas, for example, parts per million, in normal operation where the plate 77 is located in a non-constricting state as illustrated in FIGS. 5 and 6. Power supply 86 can be implemented with rechargeable batteries or replaceable batteries as would be understood by those of skill in the art.

Use of the plate 76 with opening 77 significantly reduces the gas flow through the flow or sampling path 71. This in turn reduces the amount of hydrogen sulfide needed to achieve a specific concentration. This in turn can reduce the size and power requirements of hydrogen sulfide generator 78 as well as power supply 86.

A method of calibrating a hydrogen sulfide gas sensor is also disclosed. The method includes providing a hydrogen sulfide detector and a hydrogen sulfide gas generator adjacent to the hydrogen sulfide detector. The hydrogen sulfide gas generator includes a heating element and a mixture, as described above, which is adjacent to the heating element. The method further includes heating the mixture with the heating element to release a known amount of hydrogen sulfide gas and detecting the known amount of hydrogen sulfide gas with the hydrogen sulfide detector to provide an output value from the hydrogen sulfide detector. The output value is then calibrated based on the known amount of hydrogen sulfide gas released.

In one embodiment, the heating step includes thermally decomposing the mixture to release a known amount of hydrogen sulfide gas.

In another embodiment, the mixture is encapsulated within a material selected from a polymer, a metal, and a dielectric.

In one embodiment, the metal sulfide is selected from calcium sulfide, zinc sulfide, copper sulfide, silver sulfide, sodium sulfide, carbon disulfide, polyphenylene sulfide, molybdenum disulfide, cadmium sulfide, and lead sulfide. In an additional embodiment, the solid acid is selected from citric acid, phtalic acid $C_6H_4(COOH)_2$, benzoic acid, their acidic derivatives, and polyacids, such as, polystyrene sulfonic acid, polyacrylic acid, polyphosphoric acid, polyphosphonic acid, polymaleic acid, and their acidic derivatives.

In one embodiment, the providing step includes providing an electrochemical hydrogen sulfide gas detector and a hydrogen sulfide gas generator adjacent to the hydrogen sulfide detector.

In another embodiment, the heating step includes providing a known amount of energy to the heating element to release a known amount of hydrogen sulfide.

In one embodiment, the method further includes reheating the mixture with the heating element to release a second known amount of hydrogen sulfide gas after the calibrating step; detecting the second known amount of hydrogen sulfide gas with the hydrogen sulfide detector to provide an output value from the hydrogen sulfide detector; and recalibrating the output value based on the second known amount of hydrogen sulfide gas.

In one embodiment, a time interval of at least a week occurs between the heating step and reheating step. In another embodiment, a time interval of at least a month occurs between the heating step and reheating step.

Accordingly, the description of the present invention is to be construed as illustrative only and is for the purpose of teaching those skilled in the art the best mode of carrying out the invention. The details may be varied substantially without departing from the spirit of the invention, and the exclusive use of all modifications which are within the scope of the appended claims is reserved.

We claim:

1. A self-calibrating gas sensor comprising:
   a hydrogen sulfide detector; and,
   a hydrogen sulfide generator, wherein the hydrogen sulfide generator includes a heater and a mixture of a metal sulfide and a solid acid, wherein the mixture is in proximity to the heater such that, when the heater is energized during calibration, the mixture releases an overpressure of hydrogen sulfide to the detector and such that, when the heater is not energized, the mixture releases no substantial overpressure of the hydrogen sulfide to the detector.

2. The self-calibrating gas sensor of claim 1 further including a filter that filters ambient gas to be detected by the detector.

3. The self-calibrating gas sensor of claim 1 wherein the hydrogen sulfide generator includes a gas diffusion control between the heater and the mixture on one side and the detector on the other side, and wherein the gas diffusion control controls the diffusion of hydrogen sulfide from the hydrogen sulfide generator to the detector.

4. The self-calibrating gas sensor of claim 1 further comprising a circuit that energizes the heater during calibration and that calibrates the gas sensor in response to an output of the detector during the period when the detector is provided the hydrogen sulfide.

5. The self-calibrating gas sensor of claim 1, wherein the mixture is encapsulated within a material selected from the group consisting of a polymer, a metal, and a dielectric.

6. The self-calibrating gas sensor of claim 1, wherein the metal sulfide is selected from the group consisting of calcium sulfide, zinc sulfide, copper sulfide, silver sulfide, sodium sulfide, carbon disulfide, polyphenylene sulfide, molybdenum disulfide, cadmium sulfide, and lead sulfide.

7. The self-calibrating gas sensor of claim 1, wherein the solid acid is selected from the group consisting of citric acid, phtalic acid $C_6H_4(COOH)_2$, benzoic acid, their acidic derivatives, and polyacid.

8. The self-calibrating gas sensor of claim 7, wherein the polyacid is selected from the group consisting of polystyrene sulfonic acid, polyacrylic acid, polyphosphoric acid, polyphosphonic acid, polymaleic acid, and their acidic derivatives.

9. A self-calibrating gas sensor according to claim 1, wherein said gas detector comprises an electrochemical cell.

* * * * *